United States Patent [19]

Bean et al.

[11] Patent Number: 4,949,722

[45] Date of Patent: Aug. 21, 1990

[54] METHOD FOR DETERMINING BLOOD PLATELET ADHESIVENESS

[76] Inventors: Roy Bean, P.O. Box 23, Diamond Creek 3089, Victoria; Avni Sali, 61 Mary St., Hawthorn 3122, Victoria, both of Australia

[21] Appl. No.: 408,717

[22] Filed: Sep. 18, 1989

[51] Int. Cl.$^5$ ................................................ A61B 5/00
[52] U.S. Cl. ..................................... 128/637; 128/898
[58] Field of Search ................. 128/630, 637, 897, 898

[56] References Cited

U.S. PATENT DOCUMENTS 3,969,507  7/1976  Kohri .................................... 546/158

Primary Examiner—Randall L. Green
Assistant Examiner—Randy Shay
Attorney, Agent, or Firm—Klein & Szekeres

[57] ABSTRACT

A diagnostic method or process is disclosed for determining one or more parameters which are characteristic of the adhesiveness of blood platelets of a human patient. A blood sample is collected from a venipuncture of a patient through a filter which comprises a load of glass beads or spheres placed in a medically acceptable plastic, polyvinyl or like, tube. The time is measured that it takes for a predetermined volume of the sample to be collected through the filter. For control, a blood sample is also collected without passing the sample through a filter. The number of platelets per unit volume in each sample is determined by conventional counting techniques. From the measured platelet counts and the measured time period, the rate (in platelet count per second) is calculated at which the filter apparatus retains the blood platelets of the patient. The percentage of the retained platelets as compared to the unfiltered blood sample is also calculated.

20 Claims, 1 Drawing Sheet

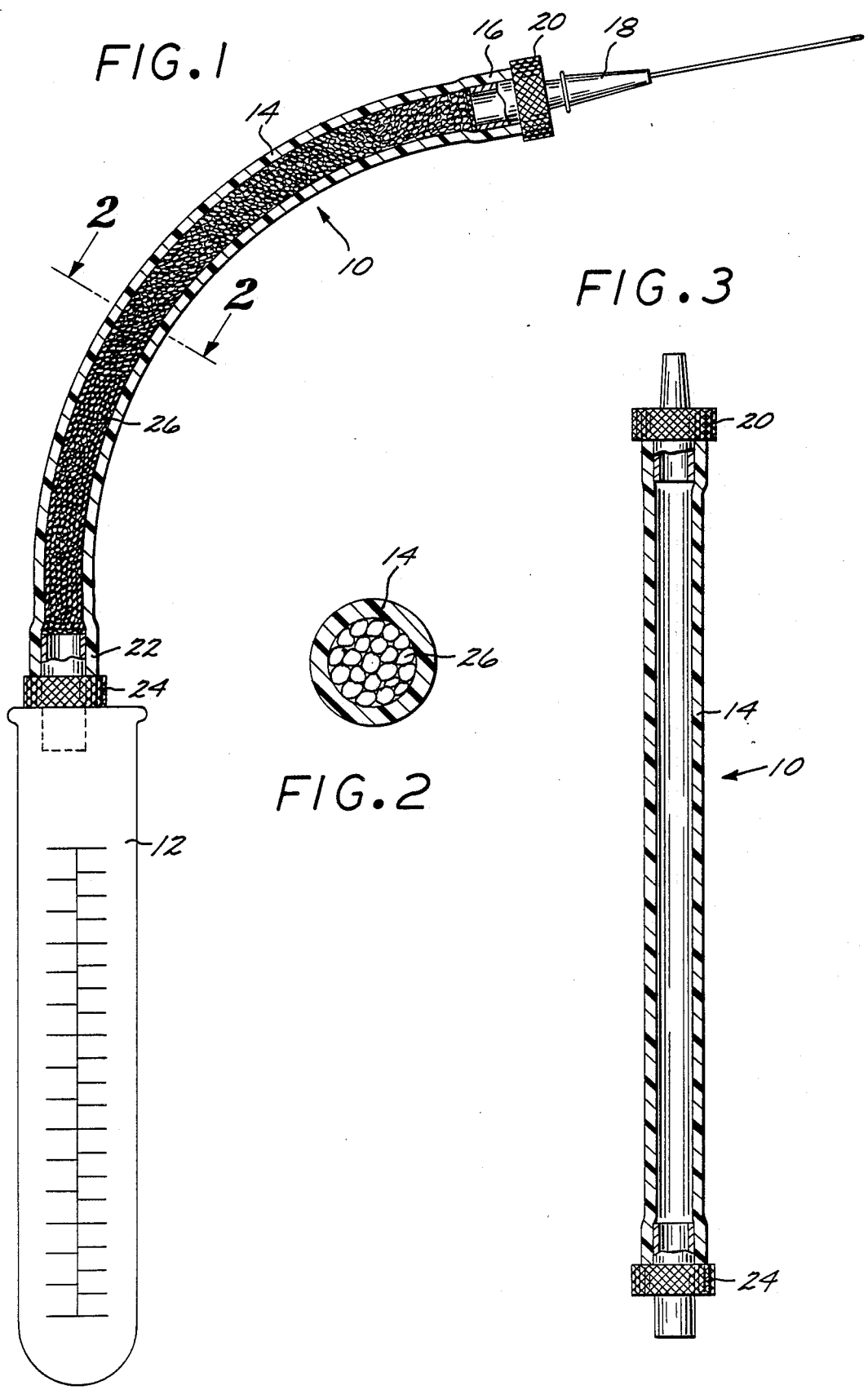

METHOD FOR DETERMINING BLOOD PLATELET ADHESIVENESS

BACKGROUND OF THE INVENTION

1. Field of the Invention

The present invention is in the field of medical testing methods and processes, and particularly in the field of diagnostic methods and processes. Still more particularly, the present invention is directed to a method or process for estimating the platelet adhesiveness of human subjects in whole blood.

2. Brief Description of the Prior Art

The role of platelet adhesiveness in blood clotting has been studied scientifically in detail. As is well known, blood clotting is a desirable occurrence for the purpose of stopping bleeding from a wounded or injured vein or artery. However, the formation of blood clots, and the associated phenomena of adhesion of platelets to the walls of vein and arteries is undesirable as it is believed to be a significant cause or factor in cardiovascular disease and death. The role of platelet adhesiveness in "desirable" blood clotting to stop blood flow from wounds, and also in the platelets, undesirable contribution to atherosclerosis and cardiovascular disease, have been studied scientifically in great detail, and have been the subject of voluminous scientific and medical literature.

An article by E. W. Salzman titled "Measurement of Platelet Adhesiveness" in the Journal of Laboratory & Clinical Medicine (November 1963) describes a "filter" containing glass beads through which a blood sample is drawn into an evacuated collection tube. The number of platelets retained by the glass beads in the "filter" is determined, in accordance with the Salzman article, by measuring the platelet count per unit volume in the blood thus collected by suction in the evacuated collection tube. The article teaches that low platelet adhesiveness is an indication of von Willebrand disease, and further that consistent or useful test data were not obtained when the blood samples are collected without suction, that is into open, rather than into evacuated, collection tubes. The Salzman article is not concerned with determination of platelet adhesiveness as an indicator of a person's state of health, condition, or degree of risk with respect to atherosclerosis and related cardiovascular disease.

Thus, in spite of the important role plaid by platelet adhesiveness in atherosclerosis and related cardiovascular disease, the prior art has developed no reliable nor simple diagnostic device or method for determining the adhesiveness or adhesion tendency of blood platelets, and thereby for determining, by a simple test, a parameter or characteristic which is indicative of a person's condition with respect to adhesion or clotting of platelets in the person's veins and arteries. The present invention, on the other hand, provides such a simple diagnostic method.

SUMMARY OF THE INVENTION

It is an object of the present invention to provide a relatively simple and inexpensive diagnostic method by which one or more parameters characteristic of the blood platelet adhesiveness of a human patient can be obtained. It is another object of the present invention to provide a diagnostic method for determining the blood platelet adhesiveness of a person, which method is suitable for routine and mass testing of people.

The foregoing and other objects and advantages are attained by a diagnostic method or process wherein blood sample is collected from a venipuncture of a patient through a filter which is formed by a load of glass beads or spheres placed in a medically acceptable plastic (polyvinyl or like) tube. The time is measured that it takes for a predetermined volume of the sample to be collected through the filter into a collecting funnel, such as a collection tube, which is exposed to ambient pressure. Control of the estimation is provided by both measuring the total platelet count on three separate samples, and by passing two separate aliquots of blood through glass bead filters. The number of platelets per unit volume in each sample is determined by conventional platelet counting techniques or procedures. From the measured platelet counts and the measured time period, one or more parameters are calculated which are indicative of the blood platelet adhesiveness of the patient.

The objects and features of the present invention are set forth in the appended claims. The present invention may be best understood, together with further objects and advantages, by reference to the following description, taken in connection with the accompanying drawings, in which like numerals indicate like parts.

BRIEF DESCRIPTION OF THE DRAWINGS

FIG. 1 is a schematic View, partly in cross section, of the apparatus used in the method or process of the present invention;

FIG. 2 is a cross-sectional view taken on lines 2,2 of FIG. 1, and

FIG. 3 is a side view, partly in cross-section of the filter apparatus used in the method or process of the present invention.

DESCRIPTION OF THE PREFERRED EMBODIMENT

The apparatus used in accordance with the present invention comprises a "filter" 10 through which a blood sample taken from a venipuncture (not shown) from a patient (not shown) is collected into a collection vessel, such as a standard hospital blood sample collecting tube 12. Although the manner of using the filter 10 is drastically different, the construction of the filter 10 is substantially similar to the filter described by Salzman in the Journal of Laboratory & Clinical Medicine article, which is cited in the introductory section of the present application for patent.

Thus, the filter 10 comprises a flexible tube 14 made from such plastic material which is medically acceptable in connection with the taking of blood samples from human patients. Medical grade polyvinyl tubing (which may be obtained from several commerical sources) is suitable for this purpose. Without intending to be limited to the herein described dimensions, it is noted that an actual filter 10, which performs well in the method of the present invention, has polyvinyl tubing 14 (obtained from Portex England) of approximately 10 cm length, and has an internal diameter of approximately 3.0 mm.

The tube 14 of the filter of the present invention is connected at one end 16 thereof through a male luer to male luer adapter 20 to a needle 18. The male luer to luer adapter 20 is available, for example, from the Beckton - Dickinson Company, U.S.A. under reorder number 3113 ml/ml. Although the exact nature of the fittings or adapters at the first end 16 of the tube 14 are not critical, it is important in accordance with the present invention to connect the first end 16 of the tube 14 to the needle 18 by which a venipuncture is made.

A second end 22 of the tube 14 is also fitted with an adapter 24, such as a VACUTRAINER luer adapter (Beckton Dickinson, France, reorder number 5731 (1004A). The precise nature of the fittings at this, second end 22 of the tube 14 are even less critical, because, through the second end 22 of the tube 14, a blood sample is allowed to collect into the blood collection tube 12 at ambient pressure. Thus, special fittings to insure maintenance of reduced pressure (vacuum) in the collection tube 12 are not required in accordance with the present invention.

The tube 14 includes a load of glass beads or spheres 26 which cause retention of blood platelets from the blood sample flowing through the filter 10. Glass beads or spheres 26, which are suitable for this purpose, are readily available from several commercial sources, such as Selbys in the State of Victoria, Australia. In this connection it is noted that the dimensions of the glass beads or spheres are critical only to the extent that the beads 26 must be sufficiently small and must have sufficiently large surface area, so as to measurably retain blood platelets from the flow of blood passing through the load of glass beads in the tube 14. It was found in accordance with the present invention that a load of approximately 1.0 g of glass beads having an approximate diameter of 0.5 mm is well suited for this purpose. The load of the glass beads 26 is retained in the tube 14 by pieces of siliconized nylon mesh (not shown) which are glued over the tip of the respective adapters.

It is an important novel feature of the present invention that a blood sample is collected from a patient through the filter by allowing the sample to simply flow into the collecting tube 12 at ambient pressure. Thus, in accordance with the present invention, an evacuated collection tube, such as a VACUTAINER tube is not used. In contrast, the prior art, exemplified by the Salzman article, teaches that acceptable results cannot be obtained without using an evacuated collection tube. Contrary to the teaching in the Salzman article, it was found in accordance with the present invention that acceptable results cannot be obtained when an evacuated collection tube (VACUTAINER) is in fact used.

Thus, in accordance with the method of the present invention, a venipuncture is made with the needle 18 connected to the filter 10. The venipuncture must be "clean", that is not contaminated with tissue fluid, and is preferably made on a large vein, e.g. the cubital fossa vein, using a standard pressure of approximately 40 mm/Hg applied by a sphygmomanometer (not shown). A predetermined volume of blood, preferably 5 ml, is then collected into the collection vessel 12, which preferably is a standard 5 ml sequestrene tube. The time that it takes for the predetermined volume (5 ml) of blood to collect in the collection tube 12 is measured and is recorded.

For comparison and control, in accordance with the present invention, at least another sample of blood is also taken from the same patient via a standard method, that is, without passing the blood sample through the filter 10 comprising a load of glass beads 26.

After the "filtered" and unfiltered blood samples have been taken, the platelet count per unit volume (per milliliter) is determined in each sample by standard laboratory techniques, which are well known in the art and need not be described here in detail. Briefly, as is well known, determination of the platelet count is performed routinely, for example, by a Coulter Counter instrument. The results described below in the present specification were actually obtained by using a Model S-plus Coulter Counter.

A single measurement of the blood sample collection time through the filter 10, and single measurements respectively of the platelet counts per unit volume for the single "filtered" and the single "unfiltered" blood samples are sufficient, in principle, to calculate the hereinafter described parameters which are characteristic of the platelet adhesiveness of a patient. Nevertheless, it is preferred in accordance with the present invention to obtain several measurements, as is described below.

Thus, two samples of a predetermined volume of blood are taken through a filter 10 from the same patient, each time using a fresh filter. Consequently, two flow time measurements and two platelet count per unit volume measurements are obtained with respect to the "filtered" blood samples of the patient.

Unfiltered blood is taken from the same patient for control, preferably three times. In this manner, three separate platelet-count-per-unit-volume measurements are obtained for the patient's "unfiltered" blood.

Because, a total of five sequestrene collection tubes 12 are filled with blood samples of the same patient, it has become customary in the diagnostic tests conducted in accordance with the present invention to fill tube numbers 1, 3 and 5 with standard (unfiltered) blood samples, and tube numbers 2 and 4 with blood samples taken through the filter 10. Accordingly, in the ensuing description P1, P3 and P5 refer to platelet counts-per-volume-units obtained from the respective three "unfiltered" control samples, and P2 and P4 refer to platelet counts per volume unit obtained from the three "filtered" blood samples. Similarly, T2 and T4 refer to the respective time periods it takes to collect the predetermined volumes (preferably 5 ml) of "filtered" blood.

The following numbers represent an actual test result obtained in the method of the present invention, conducted specifically as described above.

| | |
|---|---|
| P1 = 350,000 | (platelet count per milliliter) |
| P2 = 250,000 | T1 = 15 sec |
| P3 = 360,000 | |
| P4 = 255,000 | T4 = 16 sec |
| P5 = 355,000 | |

In connection with the foregoing it should be noted that a greater than plus or minus 10% difference between T1 and T2 suggests an error, and the desirability for repeating the tests.

The following parameters, each of which is indicative of the platelet adhesiveness of the patient, are calculated and considered in the following manner.

The time of collecting the blood samples through the filters (T2 and T4) is measured directly. The mean collection time should be less than approximately 20 seconds for patients whose platelet adhesiveness is considered normal. It is of course understood in this regard, that the longer it takes to collect a predetermined volume of sample through the filters 10, the more adhesive are the blood platelets of the patient.

Another characteristic is the number of platelets trapped by the filter per second (R). This is calculated as follows: The difference between the platelet count per unit volume of "unfiltered" blood and the platelet count per unit volume of "filtered" blood is divided by the time (seconds) required for collecting the sample. From the tests given in the actual example above, the parameter R is calculated by the following formulae.

$$R1 = (P1 - P2)/T1 \text{ and}$$

$$R2 = (P3 - P4)/T2$$

For the actual examples given above, $R1 = 6,700$ (platelets trapped by filter / second) and $R2 = 6,600$ (platelets trapped by filter / second).

From test data obtained from a substantial number of patients and healthy controls the present inventors have concluded that for the platelet adhesiveness to be normal (not excessive) the number of platelets trapped by the filter in one second should not be less than 5000 platelets / second; that is, for normal patients $R > 5,000$.

Still another characteristic of blood platelet adhesiveness is the percentage of platelets retained by the filter. (% ADH) This is defined as the difference between the platelet count (per unit volume) of "unfiltered" and "filtered" blood, divided by the platelet count of "unfiltered" blood, and multiplied by 100. For the example given above Percentage (% ADH) = 100 * (Average of [P1, P3, P5] minus Average of [P2, P4]) divided by (Average of [P1, P3, P5]) For the actual test given above, the percentage computes to 8.9. In order for the blood platelet adhesiveness to be considered normal, the ADH percentage value should be less than 80%.

It will be readily understood by those skilled in the medical and diagnostic arts that for some patients, one or more of the above-mentioned parameters may be within the normal range, whereas the remaining parameters are outside of the normal range. In this regard, the time required for the predetermined volume of blood (preferably 5 ml) to be collected through the "filter" 10, is the information which is to be given the greater significance weight when evaluating platelet adhesiveness of a patient. Actual test data for fifteen patients whose results were considered normal, and ten patients whose results were considered abnormal, are shown in the enclosed Tables. The Tables also indicate the sex and age of the patients. The test shown in the Tables were conducted using the filter apparatus specifically described in the present application as the exemplary embodiment. Furthermore, as is specifically described above, three "unfiltered" and two "filtered" blood samples were taken from each patient, for the tests.

TABLE 1

Normal Patient

| Patients No. | Sex | Age | P1 | P2 | P3 | P4 | P5 | T1 | T2 | R1 | R2 | % ADH |
|---|---|---|---|---|---|---|---|---|---|---|---|---|
| 1 | F | 31 | 341 | 166 | 317 | 162 | 369 | 12 | 13 | 14583 | 11923 | 52 |
| 2 | M | 46 | 372 | 131 | 263 | 129 | 245 | 17 | 18 | 8353 | 7444 | 50 |
| 3 | M | 71 | 258 | 139 | 244 | 153 | 253 | 15 | 14 | 7933 | 6500 | 41 |
| 4 | M | 42 | 539 | 278 | 542 | 271 | 524 | 19 | 17 | 14789 | 15941 | 49 |
| 5 | F | 83 | 447 | 201 | 411 | 192 | 414 | 16 | 15 | 15375 | 14600 | 54 |
| 6 | F | 76 | 340 | 144 | 331 | 117 | 336 | 10 | 9 | 19600 | 23778 | 61 |
| 7 | F | 50 | 156 | 102 | 160 | 81 | 158 | 10 | 12 | 5400 | 6583 | 42 |
| 8 | F | 76 | 264 | 133 | 305 | 135 | 294 | 16 | 17 | 8188 | 10000 | 53 |
| 9 | F | 62 | 244 | 139 | 260 | 153 | 253 | 11 | 11 | 9545 | 9727 | 42 |
| 10 | F | 54 | 156 | 51 | 149 | 49 | 141 | 16 | 18 | 6562 | 5555 | 66 |
| 11 | M | 43 | 329 | 119 | 317 | 125 | 315 | 17 | 18 | 12353 | 10667 | 62 |
| 12 | M | 46 | 209 | 106 | 212 | 108 | 194 | 19 | 17 | 5421 | 6117 | 48 |
| 13 | F | 38 | 115 | 57 | 115 | 49 | 122 | 15 | 14 | 3867 | 4714 | 55 |
| 14 | F | 63 | 361 | 148 | 358 | 191 | 370 | 14 | 13 | 15214 | 12846 | 53 |
| 15 | F | 45 | 287 | 96 | 322 | 111 | 267 | 17 | 16 | 11235 | 13187 | 65 |

TABLE 2

(Abnormal Patients)

| Patients No. | Sex | Age | P1 | P2 | P3 | P4 | P5 | T1 | T2 | R1 | R2 | % ADH |
|---|---|---|---|---|---|---|---|---|---|---|---|---|
| 1 | M | 46 | 279 | 85 | 275 | 102 | 259 | 25 | 24 | 7760 | 7208 | 85 |
| 2 | M | 66 | 219 | 90 | 218 | 108 | 219 | 26 | 23 | 4961 | 4783 | 55 |
| 3 | M | 44 | 210 | 91 | 189 | 88 | 202 | 27 | 25 | 4407 | 4040 | 55 |
| 4 | F | 53 | 310 | 117 | 313 | 85 | 319 | 21 | 23 | 9190 | 9913 | 68 |
| 5 | M | 80 | 148 | 52 | 133 | 68 | 153 | 28 | 26 | 3429 | 2600 | 59 |
| 6 | M | 66 | 219 | 39 | 206 | 25 | 205 | 34 | 35 | 5294 | 5171 | 85 |
| 7 | M | 67 | 154 | 40 | 146 | 46 | 157 | 24 | 22 | 5000 | 4545 | 74 |
| 8 | F | 36 | 264 | 87 | 235 | 73 | 280 | 30 | 30 | 5900 | 5400 | 69 |
| 9 | F | 46 | 177 | 22 | 157 | 38 | 141 | 24 | 22 | 6458 | 5409 | 81 |
| 10 | F | 50 | 307 | 109 | 322 | 119 | 326 | 25 | 23 | 7920 | 8820 | 64 |

The above described invention presents a relatively inexpensive and useful diagnostic method, to assist a physician's determination whether an individual is at risk for stroke or other cardiovascular disease or occurrence which is associated with blood clotting. It will be readily understood that a diagnosis of abnormally high platelet adhesiveness may suggest remedial medication and is useful in monitoring the use of aspirin, Vitamin E or other, thrombolytic agents used in the prevention or treatment of vascular disease. The method of the present invention is well adapted for routine or mass testing, whereby it is likely to become an important public health tool.

Several modifications of the above described novel diagnostic method, in terms of modifications of the apparatus used and also in terms of modifications of the steps and calculations performed, may become readily apparent to those skilled in the art in light of the present disclosure. Therefore, the scope of the invention should be interpreted solely from the following claims as such claims are read in light of the disclosure.

What is claimed is:

1. A process for measuring a platelet adhesiveness characteristic of human blood platelets, the process comprising the steps of:
   using a hypodermic needle connected to a tube which is loaded with a plurality of glass spheres, a first end of the tube being connected to the needle and a second end being exposed to normal ambient pressure, to make a venipuncture with the needle in a human subject whose blood platelet characteristic is being measured, the venipuncture causing flow of blood from the human subject through the glass sphere loaded tube;
   collecting through the glass sphere loaded tube a predetermined volume of blood sample in a container;
   measuring the time during which the predetermined volume of blood sample is collected through the glass sphere loaded tube;
   measuring the platelet count per unit of volume in the blood sample collected through the glass sphere loaded tube;
   collecting a control blood sample from the same human subject without passing the control sample through a glass sphere loaded tube, and
   measuring the platelet count per unit of volume in the control blood sample, and
   calculating from the measured time and the measured platelet counts at least one parameter characteristic of the adhesiveness of the blood platelets of the human subject.

2. The process of claim 1 wherein the step of collecting through a glass sphere loaded tube a predetermined volume of blood sample in a container, is performed twice from the same human subject and wherein the time of each collecting step is measured, and wherein the platelet counts per unit volume of each collected blood sample is also measured.

3. The process of claim 2 wherein the step of collecting a control blood sample from the same human subject without passing the control sample through a glass sphere loaded tube, is performed at least three times, and wherein the platelet count per unit volume is measured for each of the collected control samples.

4. The process of claim 1 wherein the glass sphere loaded tube is approximately 10 cm long and has an internal diameter of approximately 3 mm.

5. The process of claim 1 wherein the glass sphere loaded tube contains approximately 1.0 g of glass beads which have an average diameter of approximately 0.5 mm.

6. The process of claim 1 wherein the glass sphere loaded tube is approximately 10 cm long and has an internal diameter of approximately 3 mm, and wherein the tube contains approximately 1.0 g of glass beads which have an average diameter of approximately 0.5 mm.

7. The process of claim 1 wherein the blood sample collected through the glass sphere loaded tube and the control sample are both collected into test tubes.

8. The process of claim 1 wherein the volume of the blood sample collected through the glass sphere loaded tube and the volume of the control sample are approximately 5 ml, each.

9. A process for obtaining one or more parameters which are characteristic of the adhesiveness of the blood platelets of a human subject, the process comprising the steps of:
   collecting at ambient atmospheric pressure a predetermined volume of blood from a venipuncture on the human subject through a needle which is connected to a plastic tube having a load of miniature glass spheres, the blood being collected in a container into which the glass sphere loaded plastic tube drains;
   measuring the period of time in which the predetermined volume of blood is collected through the glass sphere loaded plastic tube;
   collecting at ambient atmospheric pressure a predetermined volume of blood from the same human subject without passing said blood through a glass sphere loaded tube;
   measuring the platelet count per unit volume of the blood sample collected through the glass sphere loaded tube and also of the blood sample collected without passing the sample through a glass sphere loaded tube, and
   calculating from said measurements at least one parameter which is characteristic of the platelet adhesiveness of the blood of the human subject.

10. The process of claim 9 wherein two samples, each substantially of the same predetermined volume, are collected from the same human subject through a glass sphere loaded tube, and wherein the time of their collection and the platelet count per unit volume of each of the two samples are measured.

11. The process of claim 10 wherein three samples, each substantially of the same predetermined volume, are collected from the same human subject without passing the samples through a glass sphere loaded tube, and wherein the platelet counts per unit volume of each of the samples are measured.

12. The process of claim 9 further comprising the step of calculating from the measured time and platelet counts the number per unit of time of platelets trapped by the glass sphere loaded tube.

13. The process of claim 9 further comprising the step of calculating from the measured time and platelet counts the percentage of platelets retained by the glass sphere loaded 14. The process of claim 9 further comprising the steps of calculating from the measured time and platelet counts the number per unit of time of platelets trapped by the glass sphere loaded tube, and the percentage of platelets retained by the glass sphere loaded tube.

15. A process for obtaining at least one parameter which is characteristic of the adhesiveness of blood platelets of human subjects, the process comparing the steps of:
   making a clean venipuncture with a needle on the human subject;
   connecting the needle with a filter, the filter comprising a tube having a load of miniature glass spheres, a first end of the filter being connected to the needle, and a second end of the tube being allowed to drain at ambient pressure into a collecting vessel;
   taking at least two samples of blood from the subject, each of the two samples being of substantially the same predetermined volume and each is taken through a fresh filter;
   measuring the time during which each sample is taken through each filter;
   measuring the platelet count per unit volume in each sample taken through the filters;

connecting a needle with a tube draining into a collecting vessel and obtaining three separate samples of blood without passing the blood through a filter; measuring the platelet count per unit volume in each of the three samples taken without a filter, and calculating from the measured times and platelets counts at least one parameter characteristic of the platelet adhesiveness of the human subject.

16. The process of claim 15 wherein the filter comprises a plastic tube having a loading of approximately 1.0 g of glass spheres of approximately 0.5 mm in diameter.

17. The process of claim 16 wherein the plastic tube is approximately 10 cm long and has an internal diameter of approximately 3 mm.

18. The process of claim 15 wherein the step of calculating comprises the step of calculating a parameter which is indicative of the number of platelets retained during a unit of time by each filter.

19. The process of claim 15 wherein the step of calculating comprises the further step of calculating another parameter indicative of the percentage of platelets retained by the filter.

20. The process of claim 15 wherein the step of calculating comprises the steps of calculating a parameter which is indicative of the number of platelets retained during a unit of time by each filter and calculating another parameter indicative of the percentage of platelets retained by the filter.

* * * * *